(12) United States Patent
Al et al.

(10) Patent No.: US 9,492,662 B2
(45) Date of Patent: Nov. 15, 2016

(54) PELVIC FLOOR MULTI-POINT PRESSURE MEASURING AND ELECTRICAL STIMULATION THERAPEUTIC APPARATUS

(75) Inventors: Guihai Al, Shanghai (CN); Meng Meng, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 283 days.

(21) Appl. No.: 14/127,640

(22) PCT Filed: Oct. 14, 2011

(86) PCT No.: PCT/CN2011/080782
§ 371 (c)(1),
(2), (4) Date: Dec. 19, 2013

(87) PCT Pub. No.: WO2013/053130
PCT Pub. Date: Apr. 18, 2013

(65) Prior Publication Data
US 2014/0128777 A1    May 8, 2014

(51) Int. Cl.
*A61B 5/103* (2006.01)
*A61N 1/36* (2006.01)

(52) U.S. Cl.
CPC .......... *A61N 1/36007* (2013.01); *A61B 5/103* (2013.01)

(58) Field of Classification Search
CPC ... A61B 5/4528; A61B 5/103; A61B 5/0053
USPC ....................................................... 600/587
See application file for complete search history.

(56) References Cited

U.S. PATENT DOCUMENTS

| 4,909,263 | A | 3/1990 | Norris | |
|---|---|---|---|---|
| 8,069,735 | B1 * | 12/2011 | Egorov | A61B 5/0053 73/862.041 |
| 2004/0054392 | A1 | 3/2004 | Dijkman | |
| 2006/0180303 | A1 * | 8/2006 | De Kimpe | E21B 47/01 166/206 |
| 2007/0185417 | A1 | 8/2007 | Mittal et al. | |
| 2009/0222058 | A1 * | 9/2009 | Craggs | A61N 1/0512 607/41 |

(Continued)

FOREIGN PATENT DOCUMENTS

| CN | 1042084 | 5/1990 |
|---|---|---|
| CN | 2889172 | 4/2007 |

(Continued)

OTHER PUBLICATIONS

Bendana, E.E. et al., "Efficacy of transvaginal biofeedback and electrical stimulation in women with urinary urgency and frequency and associated pelvic floor muscle spasm," Urol Nurs, 2009, vol. 29, No. 3, pp. 171-176.

(Continued)

*Primary Examiner* — Sean Dougherty
*Assistant Examiner* — Daniel Cerioni
(74) *Attorney, Agent, or Firm* — Foley & Lardner LLP (57) ABSTRACT

A pelvic floor treatment apparatus (100) includes a head portion (A) and a body portion (B) connected to the head portion (A) at a first end. The body portion (B) comprises: one or more pressure transducers (D1) located along a length of the body portion (B) and configured to determine pressure at one or more locations within an organ, wherein at least one of the one or more pressure transducers (D1) is selectively movable along the length of the body portion (B); and one or more electrodes (D2) configured to selectively electrically stimulate a location within the organ.

17 Claims, 8 Drawing Sheets

(56) References Cited

U.S. PATENT DOCUMENTS

2009/0270963 A1 10/2009 Pelger et al.
2012/0265044 A1* 10/2012 Broens ............... A61B 5/04882
                                                          600/373

FOREIGN PATENT DOCUMENTS

| CN | 201012088 | 1/2008 |
|---|---|---|
| EP | 2 322 110 | 5/2011 |
| WO | WO-2007/101861 | 9/2007 |

OTHER PUBLICATIONS

Chen, G.D., "Pelvic floor dysfunction in aging women," Taiwan J Obstet Gynecol, 2007, vol. 46, No. 4, pp. 374-378.
Dumoulin, C. et al., "Reliability of dynamometric measurements of pelvic floor musculature," Neurourol Urodyn, 2004, vol. 23, No. 2, pp. 134-142.
International Search Report received for PCT/CN2011/080782 mailed Jul. 26, 2012.
Lorenzo, G.M.F. et al., "Treatment of stress urinary incontinence with perineal biofeedback by using superficial electrodes," Actas Urol Esp, vol. 32, Issue 6, Jun. 2008, pp. 629-636. (Not available in English).
Poza, J.L. et al., "Trans-obturator suburethral tape for female stress incontinence: a cohort of 254 women with 1-year to 2-year follow-up," Acta Obstet Gynecol Scand, 2008, vol. 87, No. 2, pp. 232-239.
Saleme, C.S. et al., "Multidirectional Pelvic Floor Muscle Strength Measurement," Annals of Biomedical Engineering, Aug. 2009, vol. 37, No. 8, pp. 1594-1600.
The Regence Group, "Pelvic Floor Stimulation as a Treatment of Urinary Incontinence," Medical Policy Manual, Allied Health, Policy No. 4, Dec. 1, 2012, 9 pages.
Urostym, "Behavioral Therapy System—Pelvic Floor Rehabilitation," Technical Specifications, Nov. 2007, Laborie, http://www.laborie.com. 4 pages.
Verelst, M. et al., "Are fatigue and disturbances in pre-programmed activity of pelvic floor muscles associated with female stress urinary incontinence?," Neurourol Urodyn, 2004, vol. 23, No. 2, pp. 143-147.
Weng, S.S. et al., "Laparoscopic pelvic floor repair using polypropylene mesh," Taiwan J Obstet Gynecol, 2008, vol. 47, No. 3, pp. 312-317.
Whyte, T.D. et al., "Six-element sensor for measuring vaginal pressure profiles," Med. & Biol. Eng. & Comput., Mar. 1993, vol. 31, pp. 184-186.
Win Health LTD "Muscle Assessment and Muscle Rehabilitation," 2013, retrieved from http://www.win-health.com/muscle-assessment-muscle-rehabilitation.html, 4 pages.
Win Health LTD, "Pelvic Floor Stimulators," 2013, retrieved from: http://www.win-health.com/pelvic-floor.html, 5 pages.
Ximedica & IDM, "Pelvic Floor Therapeutic Apparatus," Commercial Technology Assessment Supplement, Oct. 26, 2012, 4 pages.
Ximedica & IDM, "Pelvic Floor Therapeutic Apparatus," Commercial Technology Assessment, Sep. 2012, 35 pages.
Zhang, X. et al., "Comparison of Prolift System and Gynemesh in Total Pelvic Floor Reconstructive Surgery," Chinese Journal of Clinical Obstetrics and Gynecology, 2009, vol. 10, No. 1, pp. 5-8.

* cited by examiner

PELVIC FLOOR MULTI-POINT PRESSURE MEASURING AND ELECTRICAL STIMULATION THERAPEUTIC APPARATUS

CROSS-REFERENCE TO RELATED APPLICATION

The present application is a U.S. National Phase Application under 35 U.S.C. §371 of International Application Serial No. PCT/CN2011/080782, filed on Oct. 14, 2011, the entire disclosure of which is incorporated herein by reference for any and all purposes in its entirety as if fully set forth herein.

BACKGROUND

The following description is provided to assist the understanding of the reader. None of the information provided or references cited is admitted to be prior art.

Pelvic floor dysfunction (PFD) is a common disease that affects many women, particularly as they age. Some studies have concluded that up to 40% of middle-aged and older women suffer from PFD. PFD may result in urinary incontinence and pelvic floor prolapse. In addition, PFD may occur in women both prior to and after pregnancy. PFD may occur in response to muscles of the pelvic floor weakening, becoming flaccid, or because of an impairment in the sacroiliac joint, lower back, coccyx, or hip joints. PFD often has serious effects on the physical and psychological health of patients, as well as their quality of life. Accordingly, PFD diagnosis and treatment devices and methods are in great demand.

SUMMARY

The present technology provides an illustrative pelvic floor treatment apparatus. The apparatus includes a head portion and a body portion. A handle portion may also be included. The body portion is connected to the head portion at a first end and includes one or more pressure transducers and one or more electrodes. The one or more pressure transducers are located along a length of the body portion and are configured to determine pressures along a pelvic floor of a subject. At least one of the one or more pressure transducers is selectively movable along the length of the body portion. The electrodes are configured to selectively electrically stimulate a location along the pelvic floor of the subject.

The present technology also includes an illustrative method for determining pressures within a pelvic floor of a subject. The method includes providing a pelvic floor treatment apparatus that includes a head portion and a body portion. The body portion includes one or more pressure transducers and one or more electrodes located along a length of the body portion, and at least one of the pressure transducers is selectively movable along the body portion. The method further includes arranging the pressure transducers along the body portion of the pelvic floor treatment apparatus based on dimensions of an organ of the subject and providing the pelvic floor treatment apparatus within the organ of the subject. The method also includes determining pressures at one or more locations within the organ using the one or more pressure transducers.

The present technology also includes an illustrative method for treating a pelvic floor of a subject. The method includes providing a pelvic floor treatment apparatus that includes a head portion and a body portion. The body portion includes one or more pressure transducers and one or more electrodes located along a length of the body portion, and at least one of the electrodes is selectively movable along the length of the body portion. The method also includes arranging the at least one of the electrodes along the body portion of the pelvic floor treatment apparatus based on dimensions of an organ of the subject and providing the pelvic floor treatment apparatus within the organ of the subject. The method further includes electrically stimulating identified specific areas via at least one of the one or more electrodes.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Various methods have been used to treat pelvic floor dysfunction (PFD). For example, biofeedback and electrical stimulation treatments have been proven as effective analysis and treatment methods for PFD. However, traditional biofeedback and electrical stimulation methods have generally been used only on subjects already experiencing substantial PFD symptoms. There are few examples of devices or methods for the early detection and/or prevention of PFD. In addition, traditional treatment apparatuses have suffered from an inability to perform effective individualized treatments, because such apparatuses have generally used a "one-size-fits-all" non-customizable configuration.

Described herein are illustrative methods and apparatuses for detecting and treating PFD and similar diseases. Such methods and apparatuses allow for an individualized configuration of the detection and treatment apparatus based on the specific needs of the individual subject. In addition, such methods and apparatuses allow for the simultaneous detection of pressures at multiple locations along the pelvic floor and targeted electrical stimulation of the specific identified problem areas. In an embodiment, such an apparatus includes one or more movable pressure transducers which are able to simultaneously measure pressures at different locations along a pelvic floor, e.g., along the anterior and posterior walls of the organ of a subject, and thereby determine which areas of the pelvic floor suffer from dysfunction. In an embodiment, the subject is a human subject. The apparatus may also include one or more movable electrical stimulation probes which are able to provide electrical stimulation at different locations along the pelvic floor. The location of the movable electrical stimulation probes may be adjusted with respect to the areas of dysfunction in order to provide individualized and targeted treatment of the specific areas of dysfunction.

Figure 1:
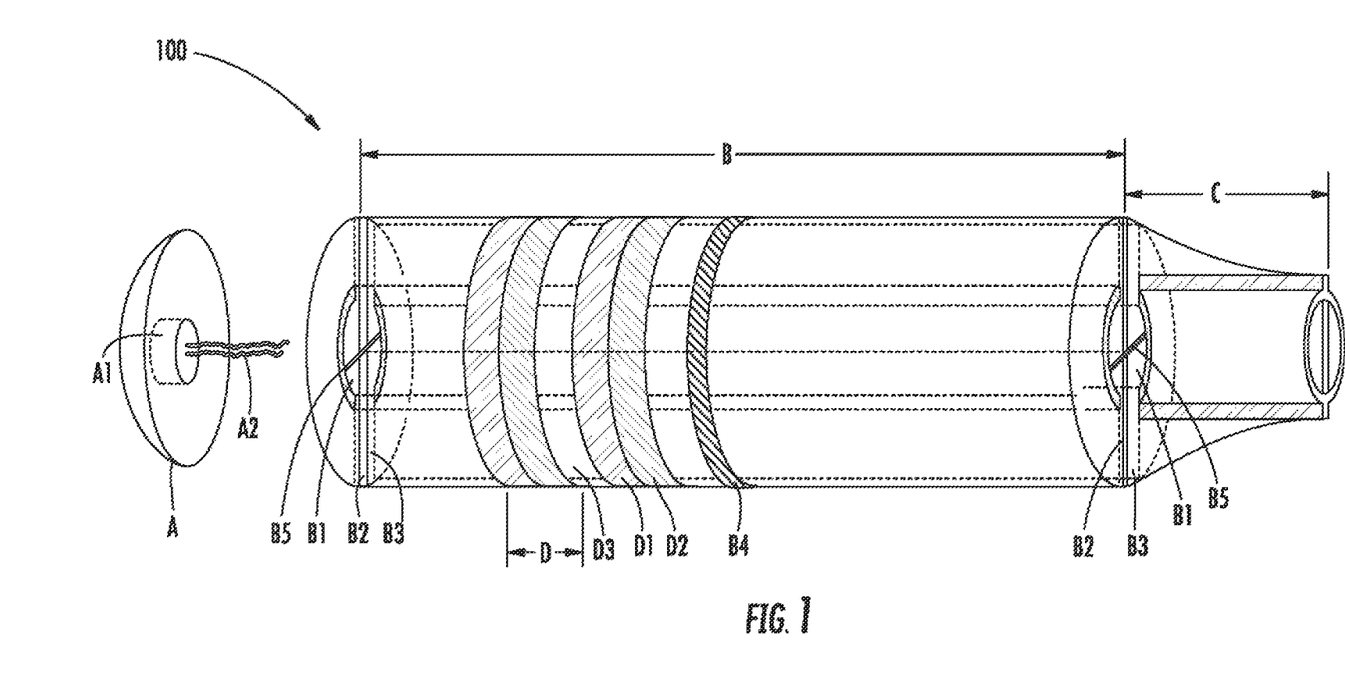
FIG. 1 depicts a pelvic floor analysis and treatment apparatus in accordance with an illustrative embodiment.

FIG. 1 depicts a pelvic floor analysis and treatment apparatus 100 in accordance with an illustrative embodiment. In an embodiment, pelvic floor analysis and treatment apparatus 100 is configured for insertion into the organ of a subject. Pelvic floor analysis and treatment apparatus 100 includes a head portion A, a body portion B, and a handle portion C. In an embodiment, head portion A is dome-shaped to facilitate insertion of pelvic floor analysis and treatment apparatus 100 into an organ of interest, e.g., a vagina. In alternative embodiments, head portion A may have alternative shapes based on the particular needs for pelvic floor analysis and treatment apparatus 100. In an embodiment, head portion A has a largest diameter of 3.5 centimeters (cm) and a thickness from an uppermost portion of head portion A to a lowermost portion of head portion A of 0.5 cm. Some studies have shown that the most reliable vaginal pressure measurements are obtained when a vagina is dilated to a range of between about 3 cm and about 4 cm. Accordingly, in an embodiment the largest diameter of head portion A may range from about 3 cm to about 4 cm. In alternative embodiments, the size of head portion A may be any size configured to comfortably fit into a vagina or other organ for which analysis and/or treatment may be needed.

Head portion A may include a pressure transducer A1 located, for example, at a topmost portion of head portion A. Pressure transducer A1 is configured to determine pressure at an innermost portion of the vagina, e.g., at a deepest portion of the vagina near the cervix. In alternative embodiments, pressure transducer A1 may be located at an alternative position of head portion A or head portion A may even omit pressure transducer A1. In an embodiment, there is only one pressure transducer in head portion A. The pressure measurements provided by pressure transducer A1 may include a determination of the abdominal pressure, the gravity of the viscera in the pelvic cavity, or any other potential pressure measurement from the innermost portion of the organ.

Head portion A also includes an electrical lead A2 that is configured to electrically connect pressure transducer A1 to a control system that is configured to control the operation of pressure transducer A1. Readings from pressure transducer A1 may thereby be communicated to the control system. In an embodiment, the control system comprises a computing system including software and/or hardware components as known to those of skill in the art. The computing system may include a processor, data storage such as a memory, one or more communication devices, one or more input devices, one or more display devices, and any other components known to those of skill in the art. In an embodiment, the control system may include a multi-channel data acquisition system configured to communicate with the pressure transducers and/or stimulation electrodes of pelvic floor analysis and treatment apparatus 100. An example of such a data acquisition system may include a 4-80 channel system as manufactured by Dewetron Company located in Graz-Grambach, Austria.

Handle portion C is positioned adjacent to body portion B and is configured to facilitate handling and manipulation of pelvic floor analysis and treatment apparatus 100. Handle portion C includes a hollow channel in physical communication with a hollow channel of body portion B and through which the electrical leads from pressure transducers and/or stimulation electrodes may pass. In another embodiment, the hollow channel may be filled with an insulating material after the electrical leads are passed through the channel. In an embodiment, handle portion C has a length of about 3 cm. In addition, the hollow channel of handle portion C may have the same or different dimensions than the hollow channel of body portion B. In alternative embodiments, the dimensions of handle portion C and its hollow channel may differ from those above according to the design needs of the particular apparatus.

In an embodiment, handle portion C may be designed so that a person may easily grip and handle pelvic floor analysis and treatment apparatus 100. According to such an embodiment, the length of handle portion C is greater than the breadth of at least one finger which may be about 1.5 cm. In an embodiment, the length of handle portion C is about 3 cm to about 4 cm, although alternative lengths are possible. Handle portion C may have any external shape that is conducive for handling. In at least one embodiment, a first end of handle portion C has a circular cross-section and has a diameter that is substantially similar to that of an end of body portion B to which the first end of handle portion C is connected. According to such an embodiment, a second end of handle portion C opposite the first end may also have a circular cross-section, but may have a diameter that is smaller than that of the first end such that the diameter of handle portion C gradually decreases from the first end to the second end.

In an embodiment, body portion B has a cylindrical shape that facilitates comfortable insertion of pelvic floor analysis and treatment apparatus 100 into the vagina or other organ of a subject. Body portion B may be constructed from sterilizable and re-usable materials having satisfactory insulation and anti-interference ability. Example materials include polycarbonate/polyethylene (PC/PE) composite plastic material, which is a high-strength insulator and helps reduce electrical interferences during measurements. Other suitable materials known to those of skill in the art may also be used. In alternative embodiments, the body portion B may have alternative shapes based on the particular needs for pelvic floor analysis and treatment apparatus 100. The average anterior vaginal wall has a length of about 7 to about 9 cm and the average posterior vaginal wall has a length of about 10 to about 12 cm. In addition, studies have shown that the most reliable vaginal pressure measurements are obtained when the vagina is dilated to about 3 cm to about 4 cm. Accordingly, in a first embodiment, body portion B has a length of about 12 cm and a diameter of about 3.5 cm, so that pelvic floor analysis and treatment apparatus 100 may be comfortably inserted into the entire vagina and so that accurate and reliable measurements may be obtained. In alternative embodiments, the size of body portion B may be any size configured to comfortably fit into a vagina or other organ for which analysis and/or treatment may be needed and for which accurate measurements and effective treatment may be administered in order to account for vaginas or organs outside of the "average" size range described above.

In an embodiment, body portion B includes a hollow channel B1, which is located within body portion B. Hollow channel B1 houses one or more electrical leads that are configured to electrically connect pressure transducers and/or stimulation electrodes of head portion A and body portion B to the control system. In an embodiment, hollow channel B1 has an annular shape including an inner diameter of about 1.6 cm, an outer diameter of about 2 cm, and a thickness of about 0.2 cm. In an embodiment, the inner diameter of hollow channel B1 may range from about 1 cm to about 2 cm, the outer diameter of hollow channel B1 may range from about 1.5 cm to about 2.5 cm, and the thickness may range from about 0.1 cm to about 0.3 cm. In alternative embodiments, the dimensions of hollow channel B1 may differ from those above according to various design needs of the particular apparatus.

Body portion B may also include a transverse partition board B2 that equally partitions body portion B into an upper portion and a lower portion and/or a longitudinal partition board B5 that equally partitions body portion B into a first side portion and a second side portion. In an embodiment, transverse partition board B2 and longitudinal partition board B5 effectively partition the cross-section of hollow channel B1 into four portions: an upper left channel; an upper right channel; a lower left channel; and a lower right channel. In an embodiment, transverse partition board B2 and longitudinal partition board B5 run the entire length of body portion B and have a thickness of about 0.15 cm. In alternative embodiments, the dimensions of transverse partition board B2 and longitudinal partition board B5 may differ from those above according to the design needs of the particular apparatus. Transverse partition board B2 and longitudinal partition board B5 may help increase the structural support of body portion B. In addition, transverse partition board B2 and longitudinal partition board B5 may partition hollow channel B1 into one or more gaps B3 through which electrical leads may be passed, thus reducing the intertwinement of such leads. In one example, longitudinal partition board B5 and longitudinal partition board B5 has a thickness of about 0.15 cm.

Body portion B may further include one or more gaps B3 through which the one or more electrical leads may pass from the pressure transducers and/or stimulation electrodes at the surface of body portion B to hollow channel B1. In an embodiment, body portion B includes four gaps B3 that extend along the entire length of body portion B and that are equally spaced so that each gap B3 is located within a respective quadrant of body portion B. In an embodiment, each gap B3 has the same width, e.g., about 0.15 cm. Gaps B3 are respectively connected to the four quadrants created partition boards B2 and B5 in hollow channel B1. In alternative embodiments, there may be fewer or less gaps B3 that may extend along the entire length or less than the entire length of body portion B according to the design needs of the particular apparatus.

Body portion B may also include a movable elastic sheet B4 disposed on the surface of body portion B. In an embodiment, movable elastic sheet B4 comprises an array of individual elements that provide a smooth material on their outermost surface and are configured to spring outward from body portion B. In addition, a layer of elastic material B8 may be disposed underneath movable elastic sheet B4 such that movable elastic sheet B4 may conform around pressure transducers D1 and/or stimulation electrodes D2 so as to provide, in combination with an outermost surface of pressure transducers D1 and/or stimulation electrodes D2, a uniform, substantially smooth surface across body portion B. According to such an embodiment, the respective elements of movable elastic sheet B4 have an approximately same width as pressure transducers D1 and/or stimulation electrodes D2 so that pressure transducers D1 and/or stimulation electrodes D2 may be moved over respective elements of movable elastic sheet B4 as desired. Such an embodiment, facilitates movement of pressure transducers D1 and/or stimulation electrodes D2 while allowing the elements of movable elastic sheet B4 adjacent to pressure transducers D1 and/or stimulation electrodes D2 to expand outward and form a uniform, substantially smooth surface across body portion B.

In an embodiment, each element of movable elastic sheet B4 can have the same size and thickness and is separate from an additional compressed layer of elastic material. This additional layer of elastic material provides an outward spring force to the elements of movable elastic sheet B4. When a respective element of movable elastic sheet B4 is not covered by pressure transducer D1 and/or stimulation electrode D2, the maximum outermost extent of the respective element is determined by a string that is connected between the respective element of movable elastic sheet B4 and an inner portion of body portion B. When a respective element of movable elastic sheet B4 is covered by pressure transducer D1 and/or stimulation electrode D2, the element of movable elastic sheet would be pushed inward from its outermost state, causing the additional layer of compressed elastic material below the respective element of movable elastic sheet B4 to become more compressed, thus producing a larger outward spring force on the respective element of movable elastic sheet B4.

In an embodiment, movable elastic sheet B4 has a thickness of about 0.2 cm. In another embodiment, movable elastic sheet B4 can have a thickness that is multiples of the width of pressure transducers D1 and/or stimulation electrodes D2, to thereby allow a respective pressure transducers D1 and/or stimulation electrodes D2 to completely cover movable elastic sheet B4. In some embodiments, the thickness of movable elastic sheet B4 may be about 0.1 cm to about 0.3 cm, and the width of the transducer and electrode vary correspondingly. In alternative embodiments, the thickness of movable elastic sheet B4 may differ from that above according to the design needs of the particular apparatus.

In an embodiment, movable elastic sheet B4 is made from sterilizable and re-usable materials having electrically-insulative and anti-electrical interference capabilities. Example materials for movable elastic sheet B4 may include polycarbonate/polyethylene (PC/PE) composite plastic material, which is a high-strength insulator and helps reduce electrical interferences during measurements. Other suitable materials known to those of skill in the art may also be used.

Body portion B also includes one or more analysis and treatment devices D distributed across the surface of body portion B. In a first embodiment, analysis and treatment devices D include both a pressure transducer D1 and a stimulation electrode D2 that extend circumferentially around body portion B. However, in alternative embodiments, analysis and treatment devices D may include only pressure transducer D1 or stimulation electrode D2. According to the first embodiment, pressure transducer D1 and stimulation electrode D2 of analysis and treatment devices D are connected in series. Pressure transducer D1 is configured to determine pressures at various locations along the pelvic floor, e.g., at various locations along the anterior and posterior walls of a vagina. In an embodiment, pressure transducer D1 is a resistance pressure strain gauge as known to those of skill in the art and as discussed in more detail below. In an embodiment, the smallest pressure transducers available are used in order to increase the number of locations along the pelvic floor which may be tested.

Various studies have indicated that pressure values are typically different in the upper, middle, and lower portions of the vagina. Accordingly, in an embodiment at least three analysis and treatment devices D are placed on at least one side of body portion B and evenly distributed along the length of body portion B. The more analysis and treatment devices D provided, the greater the measurement accuracy. However, greater numbers of analysis and treatment devices D may increase the production costs and data collecting, processing, and storage requirements for the device.

Figure 2:
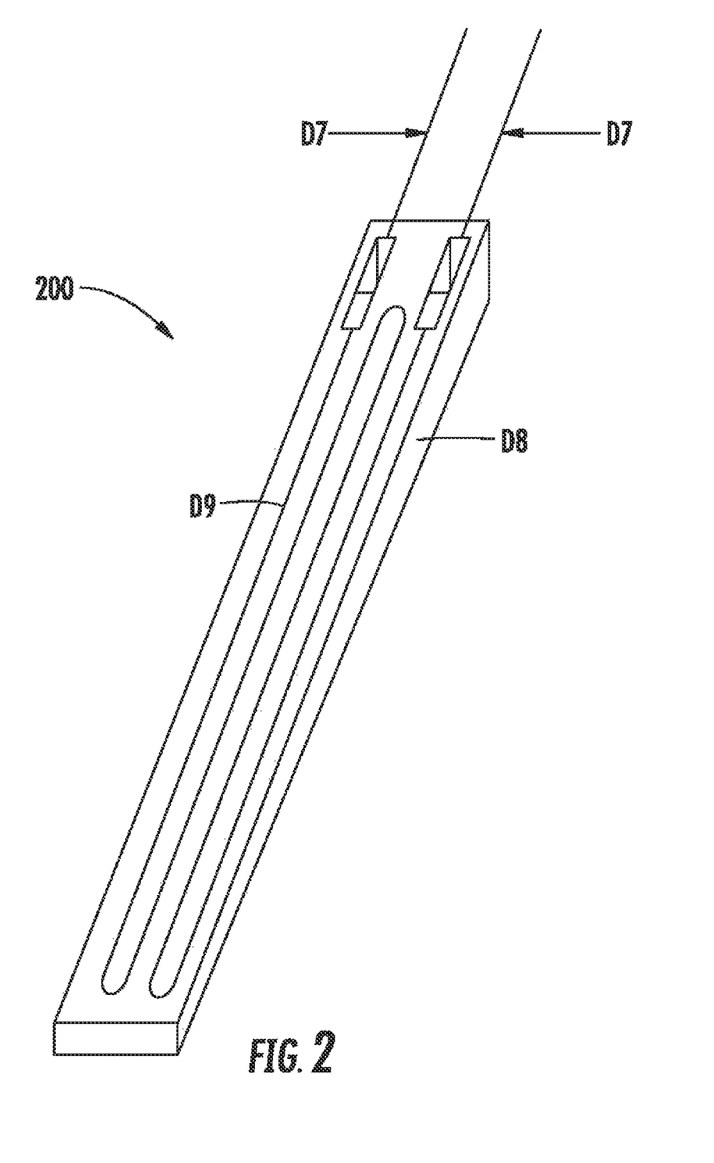
FIG. 2 depicts a resistance pressure strain gauge in accordance with an illustrative embodiment.

FIG. 2 depicts a resistance pressure strain gauge 200 in accordance with an illustrative embodiment. In an embodiment, resistance pressure strain gauge 200 is used for pressure transducer D1 of FIG. 1. Resistance pressure strain gauge 200 includes a substrate D8 and metal strain resistance wires D9. Substrate D8 may be made from an epoxy resin, polyimide, phenolic-acetal, or other suitable materials known to those of skill in the art. Metal strain resistance wires D9 may be made from steel, stainless steel, aluminum, or other suitable materials known to those of skill in the art. An example resistance strain gauge is the product model no. BA120-40AA made by Hanzhong Precision Measurement Electronics Ltd. from Hanzhong, Shanxi, China. Other resistance strain gauges known to those of skill in the art may also be used.

As pressure/force is applied to resistance pressure strain gauge 200, metal strain resistance wires D9 are stretched or otherwise deformed. The stretching/deforming of metal strain resistance wires D9 changes the geometry and thereby the electrical resistance of the wires. Accordingly, the pressure/force applied to resistance pressure strain gauge can be determined based on the quantity of change in the electrical resistance of metal strain resistance wires D9. Resistance pressure strain gauge 200 also includes electrical leads D7 which are electrically connected to metal strain resistance wires D9 and provide communication between resistance pressure strain gauge 200 and the control system, thus allowing the control system to measure the change in the electrical resistance of metal strain resistance wires D9. In an embodiment, resistance pressure strain gauge 200 has a thickness of about 0.1 cm and a width of about 0.2 cm to about 1.1 cm, although different thicknesses and widths are possible.

Stimulation electrode D2 includes an electrode plate configured to electrically stimulate a desired location along the pelvic floor of a subject. In an embodiment, stimulation electrode D2 is closely connected in series to pressure transducer D1. As such, stimulation electrode D2 is able to electrically stimulate the same location along the pelvic floor or a location very near that which is tested by its paired pressure transducer D1. In an embodiment, pulsed electrical signals are emitted from stimulation electrodes D2 in accordance with instructions from the control system. The electrical signals may have any characteristics required to provide a desired therapeutic effect. In a first embodiment of such electrical stimulation, the stimulation may be provided in 120 cycles over a total of twenty minutes, wherein each cycle includes four seconds of stimulation followed by six seconds of rest. According to such an embodiment, the frequency of electrical stimulation may be 10 Hertz (Hz), 12.5 Hz, or 15 Hz, the wave width of the electrical stimulation is approximately 200 µs and the amplitude of the electrical stimulation is approximately 12 mA to 25 mA. In an embodiment, pelvic floor analysis and treatment apparatus 100 may be designed to provide a variety of adjustable stimulation treatments. For example, in an embodiment, pelvic floor analysis and treatment apparatus 100 may be adjustable to provide an adjustable stimulation duration of 0 seconds to about 25.5 seconds, an adjustable rest duration of 0 seconds to about 25.5 seconds, and adjustable number of cycles of 0 cycles to about 3600 cycles, an adjustable frequency of about 1 Hz to about 100 Hz, an adjustable wave width of about 50 µs to about 1000 µs, and an adjustable amplitude of 0 mA to about 25 mA.

In an embodiment, stimulation electrode D1 includes a thickness of about 0.1 cm and a width about 0.2 cm to about 1.1 cm. In an embodiment, stimulation electrode D2 has a similar width to that of its paired pressure transducer D1 so that a similar location may be electrically stimulated as the location that was tested by paired pressure transducer D1.

In an embodiment, multiple analysis and treatment devices D may be located along the surface of body portion B. According to such an embodiment, adjacent analysis and treatment device D are separated by a distance D3 along the surface of body portion B. In one embodiment, analysis and treatment device D are movable/adjustable along the surface of body portion B, thus making distance D3 variable. In this way, the locations of respective pressure transducers D1 and stimulation electrodes D2 may be selectively customized to satisfy the particular needs of each individual subject. For example, the positions of pressure transducers D1 and stimulation electrodes D2 can be adjusted according to the depth of the vagina of the subject, and then the pressure of the corresponding positions of the anterior and posterior walls of the vagina may be measured and/or treated according to the customized positioning of the pressure transducers D1 and stimulation electrodes D2. In an embodiment, the analysis and treatment devices D are equally spaced along body portion B. Accordingly, the exact distance of the spacing between adjacent analysis and treatment devices D is determined based on the length of the vagina of the subject. In this way, measurement results from one subject can be easily compared to standard expected measurements results or measurement results from other patients by comparing the measurements obtained at respective locations within the vagina based on relative positions with respect to the overall length of the vagina. For example, such a comparison may be performed by comparing pressures of different patients at a first location about 15% along the length of the respective vagina, a second location about 25% along the length of the respective vagina, etc.

Analysis and treatment devices D are connected to movable heads D4 which include a protuberant portion that mates with a groove formed within a track B6. In an embodiment, track B6 can be disposed on the wall of hollow channel B1, or can be part of hollow channel B1. Track B6 can extend along the entire body portion B, and provide a plane for movable heads D4 to move thereabout. In one example, movable head D4 has a thickness of about 0.15 cm. In some embodiments, the thickness can be about 0.1 cm to about 0.2 cm depending on the design of the apparatus.

In an embodiment, a groove B7 may be disposed in track B6 and extend along the entire body portion B. In one embodiment, groove B7 has a cross section of a half circle with a diameter of about 0.1 cm. In other embodiments, the diameter of groove B7 may be about 0.1 cm to about 0.2 cm. In an embodiment, the radius of the half circle is generally smaller than the thickness (0.15 cm) of track B6, although alternative embodiments may have different configurations depending on design needs.

Movable heads D4 can be affixed to end portions of analysis and treatment devices D, and can have a thickness of about 0.15 cm. In an embodiment, the thickness of movable heads D4 is approximately the same as the width of gap B3, e.g., about 0.1 cm to about 0.2 cm based on design needs, and can be fit into gap B3. In one embodiment, movable heads D4 can have a width consistent with the width of analysis and treatment devices D, e.g., about 1.2 cm. That is, according to such an embodiment, analysis and treatment devices D may have only one movable head disposed thereon, which has a width of about 1.2 cm. In another embodiment, multiple movable heads D4 with smaller widths may be disposed on the same analysis and treatment devices D, so long as analysis and treatment devices D can be stable during movement.

Movable heads D4 can have a height of about 0.4 cm, of which the outermost 0.1 cm can be considered the thickness of analysis and treatment devices D. In an embodiment, the remaining 0.3 cm can be divided equally into three portions. The middle 0.1 cm can be designed to have a protuberant portion. The protuberant portion can have a half circular cross section that matches the half circle of groove B7. Thus, the half circle can have a diameter that is approximately the same as the diameter of groove B7, e.g., about 0.1 cm. The range of the diameter can be between about 0.1 cm and about 0.2 cm, for example, depending on the diameter of groove B7. In one embodiment, the protuberant portion can extend throughout moveable head D4, having a width of about 1.2 cm. In some other embodiments, multiple smaller protuberant portions can be disposed over movable head D4, so long as analysis and treatment devices D can be stable during movement.

In an embodiment, analysis and treatment devices D can be fixedly coupled to body portion B through moveable head D4 and the protuberant portion over moveable head D4. The protuberant portion over moveable head D4 can be designed to have a half-circular cross section, thereby reducing friction, and facilitating the sliding motion of analysis and treatment devices D over body portion B. In an embodiment, analysis and treatment device D may be moved along body portion B in steps corresponding to the thickness of respective elements of moveable elastic sheet B4. When analysis and treatment device D moves, moveable elastic sheet B4 ahead is compressed underneath analysis and treatment devices D, and an element of moveable elastic sheet B4 recoils outward from its spring force. When analysis and treatment device D is moved into a final position, adjacent elements of moveable elastic sheet B4 extend outward such that the outer surfaces of the adjacent elements are substantially even with an outer surface of analysis and treatment devices D, thereby temporarily "fixing" analysis and treatment device D into position. Thus, analysis and treatment devices D is stable, and will not become loose with left-and-right motions. In this way, analysis and treatment devices D can be fixedly coupled to body portion B, and unwanted movement of analysis and treatment devices D along body portion B may be prevented.

Figure 3A:
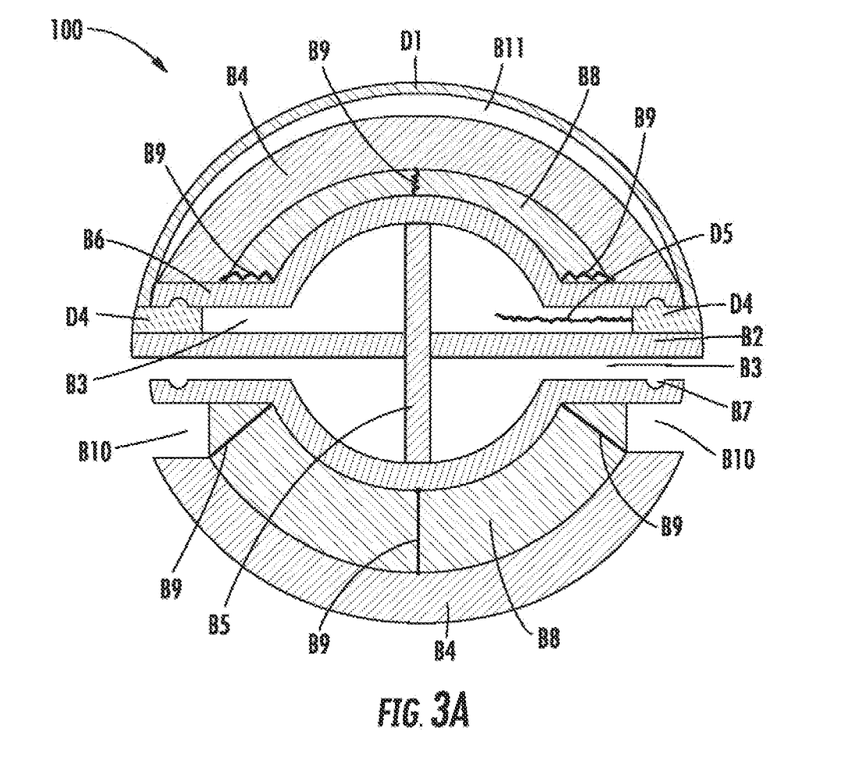
FIG. 3A depicts a cross-sectional view at a pressure strain gauge section of a pelvic floor analysis and treatment apparatus in accordance with an illustrative embodiment.

FIG. 3A depicts a cross-sectional view at a pressure strain gauge section of pelvic floor analysis and treatment apparatus 100 in accordance with an illustrative embodiment. As discussed with respect to FIG. 1 above, pelvic floor analysis and treatment apparatus 100 includes hollow channel B1 which is connected to gap B3. In addition, transverse partition board B2 and a longitudinal partition board B5 effectively partition the cross-section of hollow channel B1 into four portions: an upper left channel; an upper right channel; a lower left channel; and a lower right channel.

Electrical leads may be housed within these various portions of hollow channel B1 and may extend between the control system and respective pressure transducers D1 and stimulation electrodes D2. For example, in an embodiment, the upper right channel of hollow channel B1 may house electrical leads for pressure transducers D1 located on an upper surface of body portion B, the upper left channel may house electrical leads for stimulation electrodes D2 located on the upper surface of body portion B, the lower right channel may house electrical leads for pressure transducers D1 located on a lower surface of body portion B, and the lower left channel may house stimulation electrodes D2 located on the lower surface of body portion B. In an alternative embodiment, the electrical leads may be otherwise intermingled throughout the various portions of hollow channel B1.

Body portion B further includes one or more tracks B6 that are located along gaps B3 and that are attached to an outer surface of hollow channel B1. In an embodiment, tracks B6 extend along the entire length of body portion B. In alternative embodiments, tracks B6 may extend along only a portion of the length of body portion B. In addition, body portion B may include a plurality of tracks B6 that each extend along different portions of the length of body portion B. Tracks B6 include a depression B7 that runs along a length of the respective track and which receives a projection from movable heads D4. Movable heads D4 are connected to analysis and treatment devices D. As such, movable heads D4 may be slid along respective tracks B6 and, in turn, analysis and pressure treatment devices D may be moved along the surface of body portion B. Electrical lead D5 is connected to pressure transducer D1 and is shown extending through gap B3 and into the upper-right channel of hollow channel B1.

A compressed layer of elastic material B8 (such as elastic rubber, etc.) is positioned between movable elastic sheet B4 and the walls of hollow channel B1 so as to apply an outward force upon movable elastic sheet B4. In an embodiment, elastic material B8 is made of elastic rubber, elastic fiber, or other elastic materials known to those of skill in the art. The elastic material B8 may be made from various chemicals as known to those of skill in the art. A string B9 is used to define an outermost distance to which movable elastic sheet B4 may expand. In an embodiment, a first end of string B9 is connected to movable elastic sheet B4 and a second end of string B9 is connected to the walls of hollow channel B1. String B9 has a predetermined length that prevents an outermost surface of movable elastic sheet B4 from extending beyond a predetermined distance from the center of body portion B. In an embodiment, the predetermined distance is substantially coincident with an outermost surface pressure transducer D1 such that a smooth surface may be formed across body portion B. In an embodiment, multiple strings B9 are connected to movable elastic sheet B4 and the walls of hollow channel B1. For example, first and second strings B9 may be connected to respective end regions of movable elastic sheet B4 and a third string B9 may be connected to the center region of movable elastic sheet B4 and then respectively fixated to the walls of hollow channel B1. In an embodiment, string B9 is made of nylon yarn, although in alternative embodiments, string B9 may include any type of material known to those of skill in the art that is capable of being used as discussed below. Other example materials include nylon, polypropylene, polyester, or a mixture thereof. In an embodiment, the diameter of string B9 can be about 0.2 cm, for example, which is about the same as the thickness of movable elastic sheet B4. The length of string B9 can be the distance between the two fixation points of the ends of string B9 when movable elastic sheet B4 is in its "recoiled" state or "outermost" position, i.e., when elastic layer B8 is not compressed. For example, the length of string B9 at the middle can be about 0.45 cm (which may be the thickness of elastic layer B8 when not compressed), and the length of the string at both ends can be approximately 0.5658 cm. The ends of string B9 can be attached to movable elastic sheet B4 and hollow channel B1, respectively, using an adhesive. The adhesive may be any adhesive known to those of skill in the art for suitably attaching string B9.

As discussed above, elastic material B8 provides an outward elastic force upon movable elastic sheet B4. In an embodiment, when movable elastic sheet B4 is positioned at a maximum outermost distance as allowed by string B9, the thickness of the layer of elastic material B8 is designed to be about 0.40 cm to about 0.45 cm. In alternative embodiments, the thickness of elastic material B8 may be modified according to the design needs of the respective apparatus. For example, in other embodiments the layer of elastic material B8 may be about 0.40 cm to about 0.45 cm thick. In the embodiment, when movable elastic sheet B4 is positioned at a maximum outermost distance as allowed by string B9, a gap B10 of about 0.5658 cm is created between movable elastic sheet B4 and track B6. According to such an embodiment, when movable elastic sheet B4 is gradually moved inward for about 0.32 cm, gap B10 disappears, and movable elastic sheet B4 is completely covered by analysis and treatment device D. Both ends of movable elastic sheet B4 receive inward force from analysis and treatment device D, which is balanced by the outward spring force of movable elastic sheet B4. A gap B11 exists between movable elastic sheet B4 and analysis and treatment device D. In alternative embodiments, the size of gap B10 when movable elastic sheet B4 is positioned at a maximum outermost distance as allowed by string B9 may be modified according to the design needs of the respective apparatus.

Figure 3B:
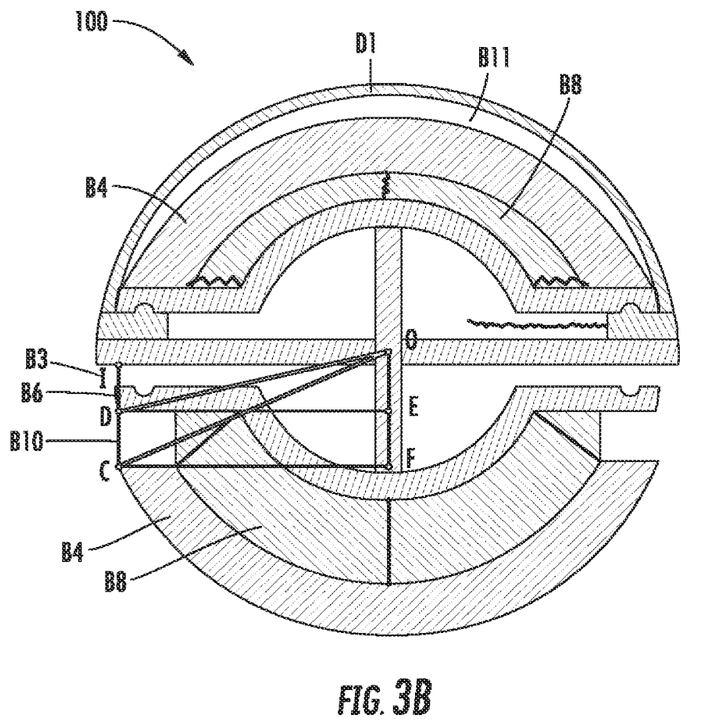
FIG. 3B depicts a cross-sectional view at a pressure strain gauge section of a pelvic floor analysis and treatment apparatus illustrating the calculation of a gap.

FIG. 3B depicts a cross-sectional view at a pressure strain gauge section of a pelvic floor analysis and treatment apparatus illustrating the calculation of a gap. To make movable elastic sheet B4 at the same level as analysis and treatment device D when in a recoiled state, to thereby have a substantially smooth surface of the apparatus, movable elastic sheet B4 should have its outer curve/surface coincide with the outer curve/surface of analysis and treatment device D. When analysis and treatment device D is ready to move toward movable elastic sheet B4 ahead, movable elastic sheet B4 is compressed inward, and finally completely covered by analysis and treatment device D, as illustrated in FIG. 3B. Gap B11 is the remaining gap after movable elastic sheet B4 is covered. During the inward motion of movable elastic sheet B4, to have it completely covered by analysis and treatment devices D, when movable elastic sheet B4 is in close proximity to track B6, the maximum span of movable elastic sheet B4 should be no greater than the distance between both ends of track B6.

As illustrated in FIG. 3B, if the inward movement distance of movable elastic sheet B4 is "x" when movable elastic sheet B4 is in close proximity to track B6, point D is at the outer most surface of track B6, on a circle with a radius of about 1.65 cm. As a result the distance between point O and point D is about 1.65 cm. The distance between point D and the horizontal diameter passing through the center of the circle O, i.e., point E, is half of the thickness of the transverse separation wall B2 plus the width of gap B3 and the width of gap B6, e.g., $OE=\frac{1}{2}*0.15$ cm+0.15 cm+0.15 cm=0.375 cm. Point C is on the outer most curve of movable elastic sheet B4, on a circle having a radius of 1.75 cm, thus the distance between points O and C is 1.75 cm. The distance between point C and the horizontal diameter passing through the center of the circle O, i.e., point F, is half the thickness of the transverse separation wall B2 plus the width of gap B3, the width of gap B6, and the width of gap D10 ("x"). As such, $OF=\frac{1}{2}*0.15$ cm+0.15 cm+0.15 cm+x=0.375 cm+x, when movable elastic sheet B4 moves inward for a distance "x" (i.e., the width of gap B10). Movable elastic sheet B4 comes in close proximity to track B6, that is $DE=CF$; because $DE^2=OD^2-OE^2$, $CF^2=OC^2-OF^2$, $OD^2-OE^2=OC^2-OF^2$, thus $1.65^2-0.37^2=1.75^2-(0.375\ cm+x)^2$, thus $x\approx 0.31827$ cm.

The larger x is, the smaller the maximum diameter of movable elastic sheet B4 is, and the easier it would be for movable elastic sheet B4 to be covered by analysis and treatment devices D. However, the larger x is, the more the stability and the comfort of the apparatus may decrease.

In addition, elastic material B8 allows movable elastic sheet B4 to be compressed inwards when an external force is applied to movable elastic sheet B4 in an inward direction. As such, when pressure transducer D1 and/or stimulation electrode D2 is moved over a given region of movable elastic sheet B4, movable elastic sheet B4 may be compressed inwards such that an outer surface of pressure transducer D1 and/or stimulation electrode D2 may form a substantially coincident and smooth surface with adjacent regions of movable elastic sheet B4 over which pressure transducer D1 and/or stimulation electrode D2 are not positioned. Accordingly, even as pressure transducers D1 and stimulation electrodes D2 are moved along the surface of body portion B, a substantially even and smooth surface along body portion B may be maintained by virtue of the combination of the outer surfaces of movable elastic sheet B4, pressure transducers D1, and stimulation electrodes D2.

Figure 4:
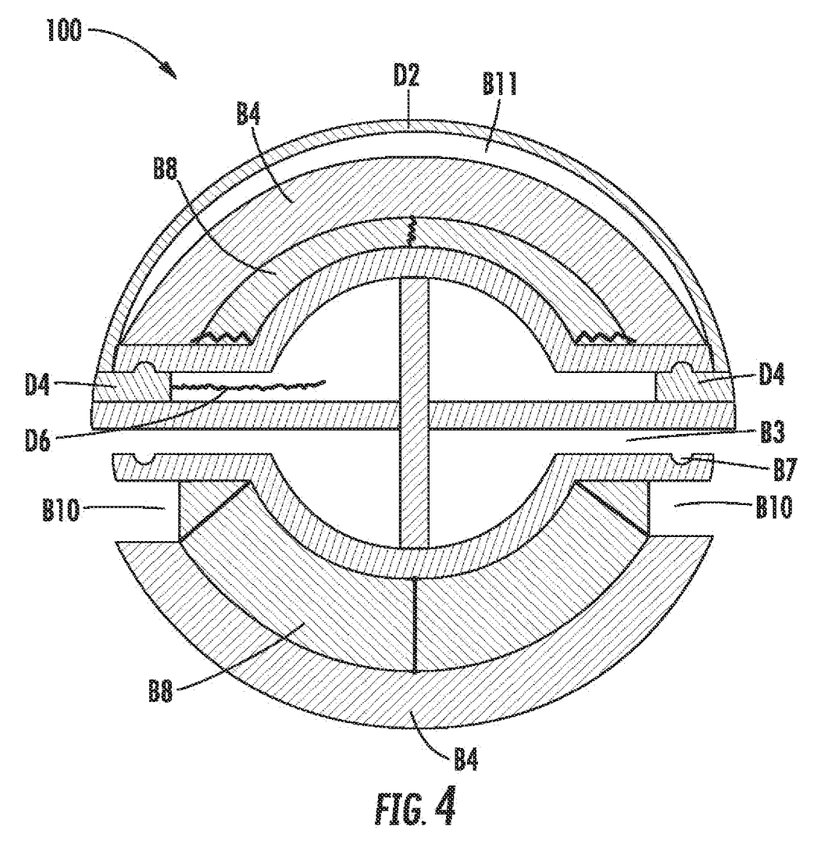
FIG. 4 depicts a cross-sectional view at a stimulation electrode section of a pelvic floor analysis and treatment apparatus in accordance with an illustrative embodiment.

FIG. 4 depicts a cross-sectional view at a stimulation electrode section of pelvic floor analysis and treatment apparatus 100 in accordance with an illustrative embodiment. FIG. 4 includes a similar configuration as FIG. 3A except that FIG. 4 illustrates an embodiment in which stimulation electrode D2 is provided in place of pressure transducer D1 on the upper half of pelvic floor analysis and treatment apparatus 100. In addition, electrical lead D6 is connected to stimulation electrode D2 and is shown extending through gap B3 and into the upper-left channel of hollow channel B1. On the lower half of pelvic floor analysis and treatment apparatus 100, no stimulation electrode D2 or pressure transducer D1 is positioned over movable elastic sheet B4. As such, the portion of movable elastic sheet B4 is in its outermost uncompressed position.

Figure 5:
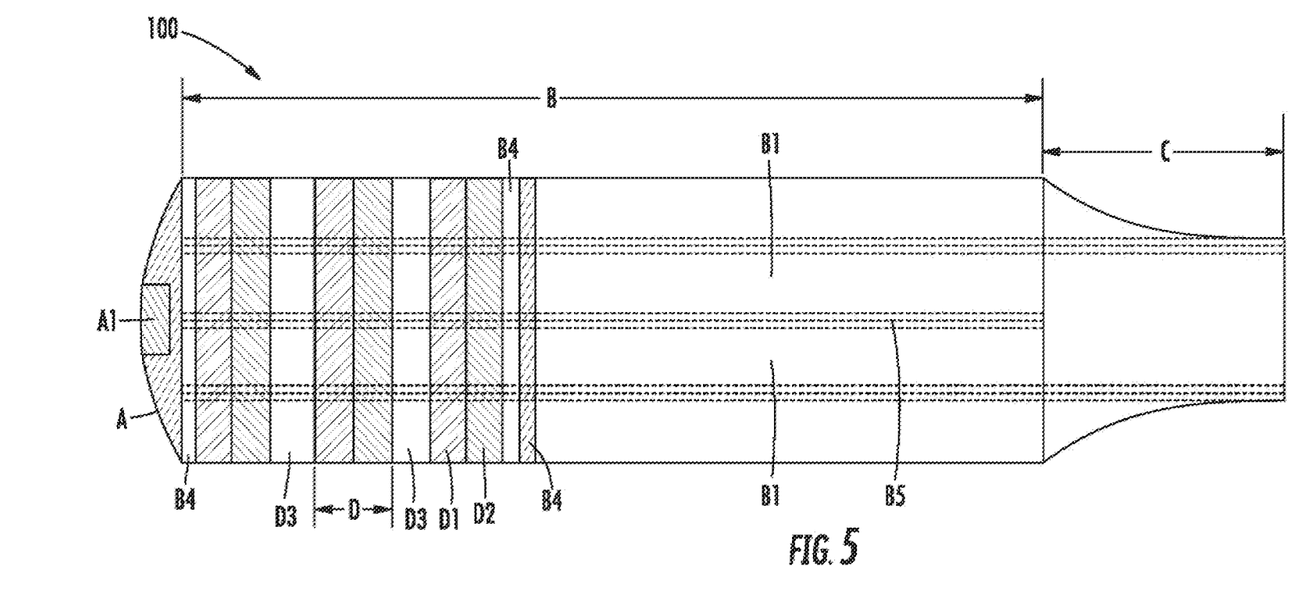
FIG. 5 depicts a top view of a pelvic floor analysis and treatment apparatus in accordance with an illustrative embodiment.
Figure 6:
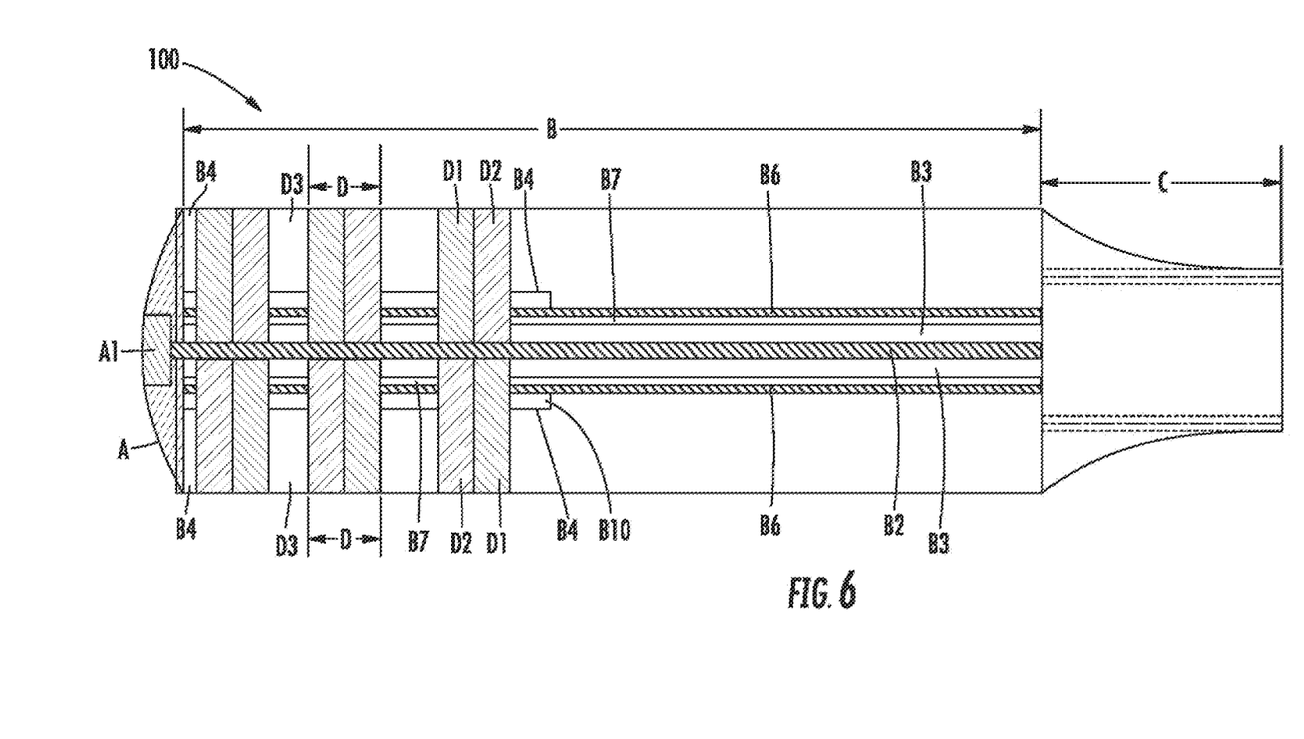
FIG. 6 depicts a lateral view of a pelvic floor analysis and treatment apparatus in accordance with an illustrative embodiment.

FIG. 5 depicts a top view of pelvic floor analysis and treatment apparatus 100 in accordance with an illustrative embodiment. FIG. 6 depicts a lateral view of pelvic floor analysis and treatment apparatus 100 in accordance with an illustrative embodiment. Pelvic floor analysis and treatment apparatus 100 includes head portion A that includes pressure transducer A1, body portion B, and handle portion C. Body portion B includes hollow channel B1 within which electrical leads are housed and longitudinal partition board B5 which extends the length of body portion B. The surface of body portion B includes movable elastic sheet B4 and one or more analysis and treatment devices D. Analysis and treatment devices D may include a pressure transducer D1 paired with a stimulation electrode D2. Adjacent analysis and treatment devices are located on the surface of body portion B and are separated by a distance D3.

In an embodiment, analysis and treatment devices D extend from a first side of body portion B to a second side of body portion B opposite the first side such that analysis and treatment devices D extend about half way around the circumference of body portion B. Accordingly to such an embodiment, a first set of analysis and treatment devices D may be located along a first half of body portion B and a second set of analysis may be located along a second half of body portion B that is opposite the first half. Such an embodiment allows for 360 degree pressure analysis and/or treatment to be simultaneously performed, e.g., pressure analysis and/or treatment may be simultaneously performed on both the anterior and posterior walls of a vagina or other organ. In an alternative embodiment, only a single set of analysis and treatment devices D is located along only one of the first half or the second half of body portion B.

In an example embodiment, body portion B includes seven analysis and treatment devices D on a top half of body portion B and seven analysis and treatment devices D on a bottom half of body portion B. Pressure transducers D1 and stimulation electrodes D2 of analysis and treatment devices D have widths of about 0.6 cm and are positioned along a body portion having a length of about 12 cm. Such an embodiment allows for a maximum average separation distance D3 between adjacent analysis and treatment devices D of about 0.6 cm.

In the embodiment of FIG. 6, a first set of analysis and treatment devices D are located along a top half of body portion B and a second set of analysis and treatment devices D are located along a bottom half of body portion B. The order of pressure transducer D1 and stimulation electrode D2 of the analysis and treatment devices D on the top half of body portion B is opposite the order of pressure transducer D1 and stimulation electrode D2 of the analysis and treatment devices D on the bottom half of body portion B. For example, for the analysis and treatment devices D on the top half of body portion B, pressure transducer D1 is nearer head portion A than its paired stimulation electrode D2. In contrast, for the analysis and treatment devices D on the bottom half of body portion B, stimulation electrode D2 is nearer head portion A than its paired pressure transducer D1. Such a configuration helps reduce or prevent the creation of 360 degree blind areas of pressure measurement or electrical stimulation, e.g., blind areas on both the anterior and posterior walls of the vagina. Such blind areas may be reduced or prevented using such a configuration by simply rotating body portion B 180 degrees within the vagina and taking additional pressure measurements and/or providing additional electrical stimulation via the rotated position of body portion B.

Figure 7:
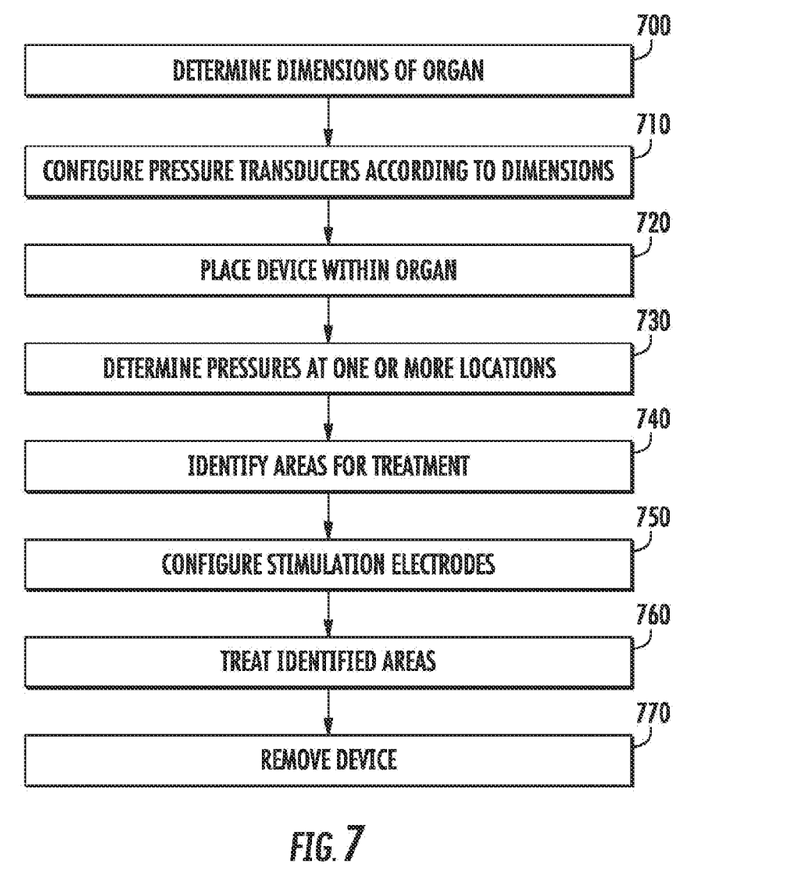
FIG. 7 depicts a method of analyzing and/or treating a pelvic floor in accordance with an illustrative embodiment.

FIG. 7 depicts a method of analyzing and/or treating a pelvic floor in accordance with an illustrative embodiment. In an operation 700, dimensions of an organ to be analyzed and treated are determined. In an embodiment, a pelvic floor of a subject may be analyzed and treated via the vagina of the subject. According to such an embodiment the lengths of the subject's anterior and posterior vagina walls are determined, respectively.

In an operation 710, a pelvic floor analysis and treatment apparatus is provided in accordance with one or more of the embodiments described above and pressure transducers are arranged along the apparatus in accordance with the determined dimensions of the organ to be analyzed. In an embodiment, the pressure transducers may be manually slid along the surface of the apparatus. In another embodiment, movement of the pressure transducers may be automated and controlled by the control system.

In an embodiment, the pressure transducers of the apparatus are arranged so that they are evenly spaced within the organ to be analyzed. In another embodiment, the pressure transducers may be moved along a surface of the pelvic floor analysis and treatment apparatus after insertion of the apparatus into the organ of interest. Such an embodiment allows the entire organ to be scanned and a more comprehensive analysis of the organ to be conducted.

In an operation 720, the pelvic floor analysis and treatment apparatus is placed within the organ to be analyzed. Using pressure transducers located on the surface of the pelvic floor analysis and treatment apparatus, pressures at one or more locations within the organ are simultaneously determined in an operation 730. Accordingly, a pressure profile of the organ being analyzed may be created which details the specific pressures produced at numerous specific locations within the organ.

Areas in need of treatment within the organ are identified in an operation 740 based on the pressure measurements from operation 730. The pressure measurements are communicated from the pressure transducers to a data acquisition system that is configured to compile and analyze the measurements. In an embodiment, the data acquisition system may include a multi-channel data acquisition system configured to analyze data from multiple channels and sensors. The data may be processed via a computing system as known to those of skill in the art. In an example embodiment, the pressure measurements from operation 730 are compared to expected/normal pressure ranges for subjects having similar background/characteristics as the subject being tested. Areas of dysfunction can be determined based on this comparison. For example, areas producing a tested pressure value that is sufficiently different than the expected or normal range of pressures may be identified as an area of dysfunction that is in need of treatment.

In an operation 750, stimulation electrodes may be arranged along the pelvic floor analysis and treatment apparatus in accordance with the locations of the identified areas in need of treatment from operation 740. For example, the stimulation electrodes are positioned along the surface of the apparatus so that, upon placement of the apparatus within the organ, the stimulation electrodes will be positioned to treat the specific identified areas in need of treatment. In an embodiment, the stimulation electrodes may be manually slid along the surface of the apparatus. In another embodiment, movement of the stimulation electrodes may be automated and controlled by the control system.

In an embodiment, the stimulation electrodes may be repositioned along the surface of the pelvic floor analysis and treatment apparatus while the apparatus is within the organ being treated. In an alternative embodiment, operation 750 may be omitted and the location of the stimulation electrodes may not be altered prior to treatment. In another embodiment, only one or more of operations 700-740 may be performed and the treatment operations 750-770 may be omitted.

In an operation 760, the specific identified areas in need of treatment are electrically stimulated via the stimulation electrodes of the pelvic floor analysis and treatment apparatus. In an embodiment, a pulsed electrical signal or other therapeutic electrical signal is applied to the specified identified areas in need of treatment. In an embodiment, the apparatus includes a plurality of stimulation electrodes and only a subset of these stimulation electrodes are used to treat the identified areas in need of treatment. The stimulation electrodes and applied electrical signal may be controlled via a control/computing system as known to those of skill in the art and that is connected to the stimulation electrodes via electrical leads. In an operation 770, the pelvic floor analysis and treatment apparatus is removed from the treated organ.

EXAMPLE

The above-described apparatus may be used in females who have a potential for pelvic floor issues, particularly patients that have had multiple abortions, births, and those with lower levels of estrogen during menopause or post menopause. Treatment may target defective positions along the pelvic floor as determined by analysis using pressure transducers and comparison to healthy expected pressures. In an embodiment, a pelvic floor analysis and treatment apparatus is used for pressure measurement of healthy women with normal pelvic floors (e.g., where a B-mode ultrasonography of pelvic cavities is normal, without bulge of paries anterior vaginase, douglascele, or uterine prolapse). For a sufficiently large sample, each group may need at least 100 samples. The normal range of pressure in various pelvic floor positions of normal females of different age groups can thereby be determined prior to analysis and treatment of a patient. Based on statistics, it can be specified that the 95% likelihood range of the overall average is the normal range, and that values outside the range are considered small probability events, or abnormal.

To reduce errors in establishing this "normal value range," other factors that would affect the pelvic floor pressure should be reduced, including age, and histories of vaginal deliveries. The four groups are divided based on that, through research, it was found that for women younger than 35 years old, whether they have vaginal delivery histories, there are no large variations in their pelvic floor pressures, and thus can be grouped as one group. For women older than 36 years old, there is little research on whether there was vaginal delivery would affect the pelvic floor pressure. Thus, those with and without vaginal delivery histories can be divided into different groups. In addition, early research has shown that after menopause, the level of estrogen drops, and the pelvic floor tissues become loose, greatly lowering the pelvic floor pressure. Thus, women after menopause should be grouped into one group. Treated women can therefore be placed into one of the following groups: women who are younger than 36 years, women 36 years old or older until menopause and without vaginal child deliveries, women 36 years old or older until menopause and with vaginal deliveries, and postmenopausal women. The expected measurements for women within each of these groups will vary and thus grouping of women within one of the above groups helps narrow the expected range of measurements and provides a more accurate and detailed basis for analysis. A normal range of pressure values at different parts of pelvic floors of different normal women at various ages is collected and established to use as an expected range of values to compare to subsequent tests. Therefore, the pressure of pelvic floors of women at different ages can be screened and compared to the normal expected range of pressure values at different parts of the pelvic floor.

If the measured pressure value of the subject significantly differs from the value of the expected normal range, that is, a 95% likelihood range of the overall average, it may be determined that there is a defect at the part producing the significant difference. In alternative embodiments, a different range may be used to determine occurrences of abnormalities. Because the research demonstrates that pelvic floor dysfunction (PFD) develops incrementally, before the dysfunction appears across the entire pelvic floor, the dysfunction may be detected early by virtue of pathological changes at various parts of the pelvic floor tissue. Such changes are typically indicated by flaccid tissue that results in a decreased pressure in the specific area of the pelvic floor. In this way, the position of the specific defect in the pelvic floor can be located and an early intervention can be given to the potential PFD subject (individuated electrical stimulation therapy) to prevent PFD.

In an embodiment, a treatment method may proceed as follows: The specific portions of the pelvic floor where defects appear being discovered according to the above pressure measuring procedure. (1) The subject is laid down flat on an examination bed, and the lengths of the vaginal forward and backward walls can be measured. Because an apparatus according to one embodiment disclosed herein can have 7 movable pressure probes disposed therein, based on the measured values, the 7 movable pressure probes can be distributed uniformly throughout the vaginal walls. For example, one probe is disposed at the inner most portion of the vagina, one probe is disposed at the outer most portion of the vagina, and the remaining 5 probes are uniformly distributed throughout the length of the vagina. (2) After the pressure probes are adjusted, the probes can be horizontally placed inside the vagina. The pressures at the different points are measured respectively when the subject is relaxed and when the anus is contracted. The measured data can be saved to a computer. The pressure values measured when the subject is relaxed reflect the baseline pelvic floor pressure values of the subject. The pressure values measured when the anus is contracted reflect the pelvic floor muscle strength of the subject. During the anus contraction movement, the subject may be asked to avoid using belly pressure. A first probe disposed at the end of the apparatus can be used to monitor the belly pressure, and can be used to observe the subject to direct the subject to perform anus contraction, avoiding belly pressure, to make the measurements more accurate. (3) The measured pressure values at the different locations and during the relaxed state and the anus contraction can be compared with the predetermined standard/expected reference values for normal healthy women in the patients associated group. If the measured values are within the 95% likelihood range of the overall average, then the values are considered normal. However, if the measured values are outside this range, they are considered abnormal, and the patient is considered to exhibit pelvic floor dysfunction.

Movable electrode slices on the probes are adjusted to aim at the specific portions of the pelvic floor where defects appear. Based on the pressure measurement procedures described above, the specific defective positions in the pelvic floor can be determined. That is, the positions of the pressure sensors corresponding to the "abnormal values" are known. Thus, the electrical stimulation probes coupled to the pressure sensors can be moved to the defective positions for targeted treatment. The specific movement procedures can include compressing respective elements of movable elastic sheet B4 and moving analysis and treatment devices D over the respective elements of movable elastic sheet B4 such that analysis and treatment devices D are move into a desired position. Electrical stimulation treatment can be performed at the specific desired position and the dysfunction areas of the pelvic floor may thereby be treated.

An example scenario of electrically stimulating the pelvic floor muscle is as follows: a cycle of 4 seconds for stimulation and 6 seconds for rest, 120 cycles, that is, 20 minutes totally; the frequency of electrical stimulation can be 10 Hz, 12.5 Hz, and 15 Hz; the wave width of electrical stimulation is 200 μs; the strength of electrical stimulation is between 12 mA and 25 mA, adjusted according to the tolerance of the patient; the treatment cycle is a week, five times per week, the next cycle being carried out after 2 days off, and the pressure condition of the pelvic floor will be evaluated once more after about 8 cycles in total to see the effects of the treatments. A large number of studies have shown that electrical stimulation treatments for the pelvic floor coordinated with anal contraction exercises can effectively exercise the muscles of the pelvic floor and thereby treat PFD.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A pelvic floor treatment apparatus, the apparatus comprising:
   a head portion; and
   a body portion connected to the head portion at a first end, wherein the body portion comprises:
      one or more pressure transducers located along the body portion and configured to determine pressures at one or more locations within an organ;

a movable head connected to at least one of the one or more pressure transducers; and a track extending along a length of the body portion, wherein the movable head engages the track such that the movable head and the at least one of the one or more pressure transducers are selectively movable along the track and along the length of the body portion; and one or more electrodes configured to selectively electrically stimulate a location within the organ, wherein the track extends from a first location on the body portion proximate the head portion to a second location on the body portion, and wherein the second location is a greater distance from the head portion than the first location is from the head portion.

2. The pelvic floor treatment apparatus of claim 1, further comprising a handle portion connected to the body portion at a second end opposite the first end.

3. The pelvic floor treatment apparatus of claim 1, wherein the body portion further comprises a movable elastic sheet configured to provide, in combination with respective surfaces of the one or more pressure transducers and respective surfaces of the one or more electrodes, a smooth surface across the body portion.

4. The pelvic floor treatment apparatus of claim 3, further comprising an elastic material configured to push the movable elastic sheet outward from a center of the body portion, and wherein at least a first portion of the movable plastic sheet is disposed between the one or more pressure transducers and a center of the body portion and at least a second portion of the movable plastic sheet is disposed between respective pressure transducers of the one or more pressure transducers to form the smooth surface across the body portion.

5. The pelvic floor treatment apparatus of claim 1, wherein the body portion further comprises a hollow channel and one or more leads electrically connected to the one or more pressure transducers or the one or more electrodes, and wherein the one or more leads are disposed within the hollow channel.

6. The pelvic floor treatment apparatus of claim 1, wherein at least one of the one or more pressure transducers comprises a resistance pressure strain gauge.

7. The pelvic floor treatment apparatus of claim 1, wherein each of the one or more pressure transducers is paired with one of the one or more electrodes such that the each pressure transducer is disposed adjacent its paired electrode, and wherein the body portion further comprises:

a first pressure transducer and an adjacent first electrode disposed on a first side of the body portion, wherein the first pressure transducer is located nearer the head portion than the adjacent first electrode; and a second pressure transducer and an adjacent second electrode disposed on a second side of the body portion opposite the first side of the body portion and directly across from the first pressure transducer and the adjacent first electrode, wherein the second adjacent electrode is located nearer the head portion than the second pressure transducer.

8. The pelvic floor treatment apparatus of claim 1, wherein the one or more transducers are evenly spaced across the length of the body portion.

9. The pelvic floor treatment apparatus of claim 2, wherein the track extends along an entire length of the body portion between the head portion and the handle portion.

10. The pelvic floor treatment apparatus of claim 1, wherein the movable head comprises a protuberant portion that mates with a groove formed in the track.

11. The pelvic floor treatment apparatus of claim 1, wherein the head portion comprises a pressure transducer located at a topmost portion of the head portion and configured to determine a pressure at a top of the organ.

12. The pelvic floor treatment apparatus of claim 1, wherein the body portion further comprises an analysis and treatment device that includes the at least one of the one or more pressure transducers paired with one of the one or more electrodes, and wherein the movable head is affixed to the analysis and treatment device such that the analysis and treatment device is configured to slide along the track.

13. The pelvic floor treatment apparatus of claim 5, wherein the track is disposed on a wall of the hollow channel.

14. The pelvic floor treatment apparatus of claim 1, wherein the body portion further comprises a transverse partition board that partitions the body portion into an upper portion and a lower portion.

15. The pelvic floor treatment apparatus of claim 14, wherein the body portion further comprises a longitudinal partition board that partitions the body portion into a first side portion and a second side portion.

16. The pelvic floor treatment apparatus of claim 15, wherein the transverse partition board is perpendicular to the longitudinal partition board.

17. The pelvic floor treatment apparatus of claim 15, wherein the transverse partition board and the longitudinal partition board together form four gaps extending the length of the body portion.

* * * * *